United States Patent
Bartning et al.

(10) Patent No.: US 7,935,098 B2
(45) Date of Patent: May 3, 2011

(54) APPLICATOR FOR INTRAVAGINAL DEVICES

(75) Inventors: Michelle Bartning, Fremont, CA (US); Mari Hou, Hoboken, NJ (US); Raymond J. Hull, Jr., Hampton, NJ (US); Kirsten Freislinger Luehrs, Palo Alto, CA (US); Scott M. Russell, San Jose, CA (US); Paul B. Swick, Lebanon, NJ (US); Pramod Mavinkurve, Princeton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 121 days.

(21) Appl. No.: 12/059,607

(22) Filed: Mar. 31, 2008

(65) Prior Publication Data

US 2009/0247928 A1    Oct. 1, 2009

(51) Int. Cl.
*A61F 13/15* (2006.01)
*A61F 13/20* (2006.01)

(52) U.S. Cl. ............ 604/385.17; 604/13; 604/904
(58) Field of Classification Search ........... 604/13–18, 604/385.17–385.18, 904
See application file for complete search history.

(56) References Cited

U.S. PATENT DOCUMENTS

| | | | |
|---|---|---|---|
| 3,643,661 A | 2/1972 | Crockford | |
| 3,706,311 A | 12/1972 | Kokx et al. | |
| 4,048,998 A * | 9/1977 | Nigro | 604/14 |
| 4,143,656 A | 3/1979 | Holmes | |
| 4,198,978 A | 4/1980 | Nigro | |
| 4,398,532 A | 8/1983 | Sweeney, III | |
| 4,447,222 A | 5/1984 | Sartinoranont | |
| 5,041,080 A * | 8/1991 | Shimatani et al. | 604/13 |
| D349,339 S * | 8/1994 | Youtsler et al. | D24/133 |
| 5,483,976 A | 1/1996 | McLaughlin et al. | |
| 5,618,256 A | 4/1997 | Reimer | |
| 5,659,934 A | 8/1997 | Jessup et al. | |
| 5,785,640 A | 7/1998 | Kresch | |
| 5,807,372 A | 9/1998 | Balzar | |
| 5,873,971 A | 2/1999 | Balzar | |
| 6,645,136 B1 | 11/2003 | Zunker et al. | |
| 6,648,846 B2 * | 11/2003 | Binner et al. | 604/15 |
| 6,695,763 B2 | 2/2004 | Zunker | |
| 6,739,340 B1 | 5/2004 | Jensen | |
| 6,969,380 B1 | 11/2005 | Zunker | |
| 2004/0077924 A1 | 4/2004 | Zunker | |
| 2004/0078013 A1 | 4/2004 | Zunker | |

(Continued)

FOREIGN PATENT DOCUMENTS

EP    104039 A    3/1984

(Continued)

*Primary Examiner* — Michele Kidwell (57) ABSTRACT

An applicator for intravaginal devices includes an elongate handle, an insertion sleeve, and an intravaginal device support member. The elongate handle has an open first end that defines a cavity extending into the handle. The insertion sleeve extends from the open first end of the handle; it is arranged and configured to slide into the cavity of the handle and to accommodate an intravaginal device; and it has associated therewith a trigger. The intravaginal device support member is disposed in the cavity of the handle; it is operatively connected to the handle; and it has a bearing surface disposed proximate the open first end of the handle. The applicators are useful to ensure that intravaginal devices are placed in the appropriate position to be effective.

9 Claims, 7 Drawing Sheets

| U.S. PATENT DOCUMENTS | | | FOREIGN PATENT DOCUMENTS | | |
|---|---|---|---|---|---|
| 2004/0122745 A1 | 6/2004 | Hantke et al. | EP | 1688112 A | 8/2006 |
| 2005/0096721 A1 | 5/2005 | Mangin | GB | 557035 A | 11/1943 |
| 2006/0004320 A1 | 1/2006 | Berg et al. | WO | WO 95/05790 A | 3/1995 |
| 2007/0128254 A1 | 6/2007 | Heuer et al. | WO | WO 00/67662 A | 11/2000 |
| 2007/0203429 A1 | 8/2007 | Ziv | WO | WO 02/26160 A | 4/2002 |
| 2008/0009662 A1 | 1/2008 | Bartning et al. | WO | WO 2004/103213 A | 12/2004 |
| 2008/0009663 A1 | 1/2008 | Bartning et al. | WO | WO 2005/087153 A | 9/2005 |
| 2008/0009664 A1 | 1/2008 | Bartning et al. | WO | WO 2005/087154 A | 9/2005 |
| 2008/0009666 A1 | 1/2008 | Bartning et al. | WO | WO 2006/005009 A | 1/2006 |
| 2008/0009814 A1 | 1/2008 | Bartning et al. | WO | WO 2006/097935 A | 9/2006 |
| 2008/0009931 A1 | 1/2008 | Bartning et al. | WO | WO 2007/146270 A | 12/2007 |
| 2008/0033230 A1 | 2/2008 | Bartning et al. | WO | WO 2009/044394 A | 4/2009 |
| 2008/0033231 A1 | 2/2008 | Bartning et al. | | | |
| 2008/0281149 A1 | 11/2008 | Sinai et al. | | | |

\* cited by examiner

APPLICATOR FOR INTRAVAGINAL DEVICES

BACKGROUND OF THE INVENTION

1. Field of the Invention

The present invention relates to an applicator for intravaginal devices. The applicator is useful for placing the device in the vagina in the correct position to enable the device to function. The applicator is designed to be used with tampons or urinary incontinence devices.

2. Description of the Prior Art

Tampons are absorbent articles that are inserted into a woman's vagina to absorb blood while she is menstruating. Urinary incontinence devices are inserted into a woman's vagina to reduce or inhibit urinary incontinence. Applicators may be used to ease the insertion of urinary incontinence devices and tampons. Applicators typically include a generally cylindrical barrel for holding the tampon or device and placing in the vagina, and a plunger for expelling the device or tampon into the vagina. Cardboard and plastic applicators are known in the art.

The placement and orientation of a urinary incontinence device is important in enabling the device to function properly. For some devices, it is important that the device is deployed in a position where pressure is applied to the urethra at the neck of the bladder. As some urinary incontinence devices expand to generate force, it is important that the device is oriented so that the force is directed toward the urethra. Therefore, the urinary incontinence device needs to be deployed in the right location.

Tampon applicators are known to contain finger grip portions. World Patent Application number WO2006/005009A1 discloses an applicator with indicia for low placement in the vagina on the barrel.

Many such tampon applicators are barrel and plunger type applicator systems in which the barrel is held in place while the tampon is expelled from the barrel by pushing it out of the insertion end of the barrel. Absorbent intravaginal tampons generally do not expand rapidly upon expulsion. Therefore, movement of the tampon into the vagina generally does not provide the opportunity to damage the tender vaginal tissues. However, devices designed to expand rapidly into a significantly larger diameter structure may provide a greater opportunity for injury to vaginal tissues. Therefore, there is a continuing need for improved applicators that deploy tampons or incontinence devices in the vagina, especially those that are capable of rapid expansion.

SUMMARY OF THE INVENTION

It has been discovered that improved applicators that deploy tampons or incontinence devices in the vagina can be produced that limit the need to move expanding or expanded structures within the vagina. Several ways to achieve this are disclosed herein.

In one aspect of the invention, an applicator for intravaginal devices includes an elongate handle, an insertion sleeve, and an intravaginal device support member. The elongate handle has an open first end that defines a cavity extending into the handle. The insertion sleeve extends from the open first end of the handle; it is arranged and configured to slide into the cavity of the handle and to accommodate an intravaginal device; and it has associated therewith a trigger. The intravaginal device support member is disposed in the cavity of the handle; it is operatively connected to the handle; and it has a bearing surface disposed proximate the open first end of the handle. The applicators are useful to ensure that intravaginal devices are placed in the appropriate position to be effective.

In another aspect of the invention, an applicator for intravaginal devices includes an elongate tubular handle, an elongate insertion sleeve, and an intravaginal device support member. The tubular handle has an open first end and a longitudinal slot. The insertion sleeve has a base portion contained within the handle, and the sleeve extends from the open first end of the handle, terminating in an insertion end disposed distal the handle. The insertion sleeve is arranged and configured to slide into the tubular handle and to accommodate an intravaginal device. There is a trigger operatively connected to the base portion of the insertion sleeve. The intravaginal device support member is disposed in the cavity of the handle; it is operatively connected to the handle; and it has a bearing surface disposed proximate the open first end of the handle. The applicators are useful to ensure that intravaginal devices are placed in the appropriate position to be effective.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF PREFERRED EMBODIMENTS

As used herein the specification and the claims, the term "trigger" and variants thereof relate to a device used to activate a mechanism; in this case, to activate the movement of the insertion sleeve.

With reference to the figures, applicators 10 according to the present invention include an elongate handle 12, an insertion sleeve 14, and an intravaginal device support member 16. The handle 12 has an open first end 18 that defines a cavity 20 extending into the handle. The intravaginal device support member 16 is disposed in the cavity 20 of the handle 12, and it is operatively connected to the handle 12, e.g., through connecting member 22 shown in FIG. 2 at the base 24 of the support member 16. A bearing surface 26 of the support member 16 is disposed proximate the open first end 18 of the handle 12.

Figure 2:
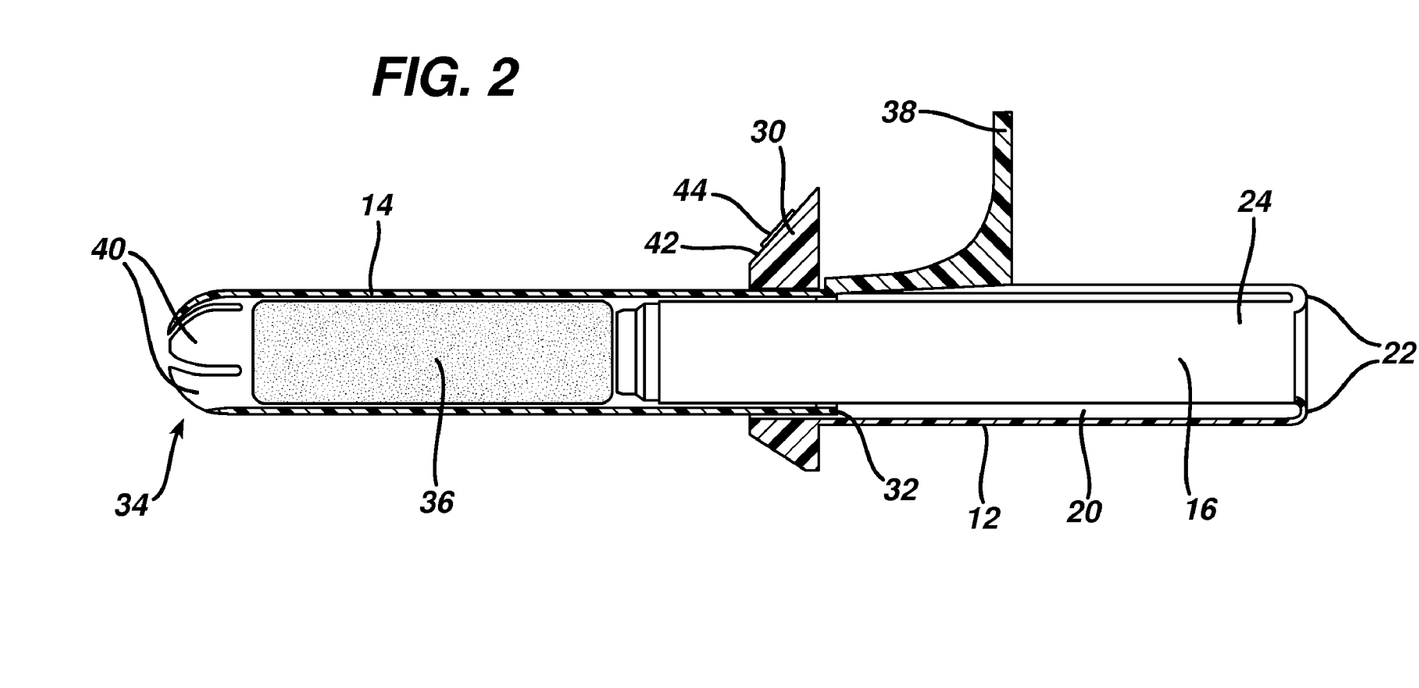
FIG. 2 is a cross-section of the applicator of FIG. 1, taken along line 2-2.
Figure 3:
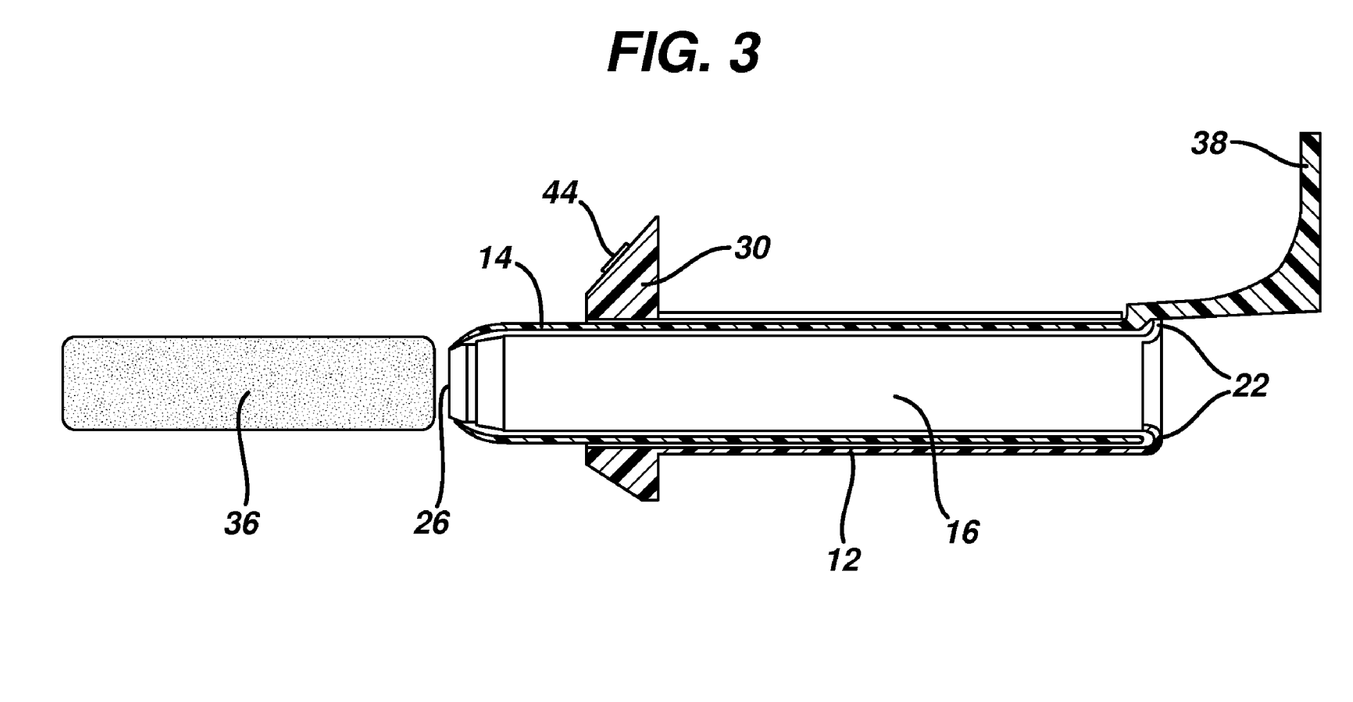
FIG. 3 is a cross-section of the applicator of FIGS. 1 and 2, after expulsion of a device contained therein.
Figure 4:
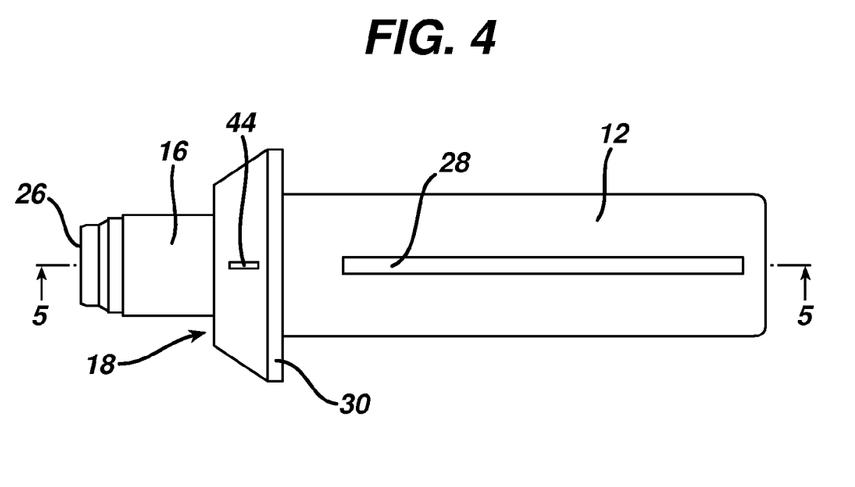
FIG. 4 is a plan view of the handle of an applicator according to the present invention.
Figure 5:
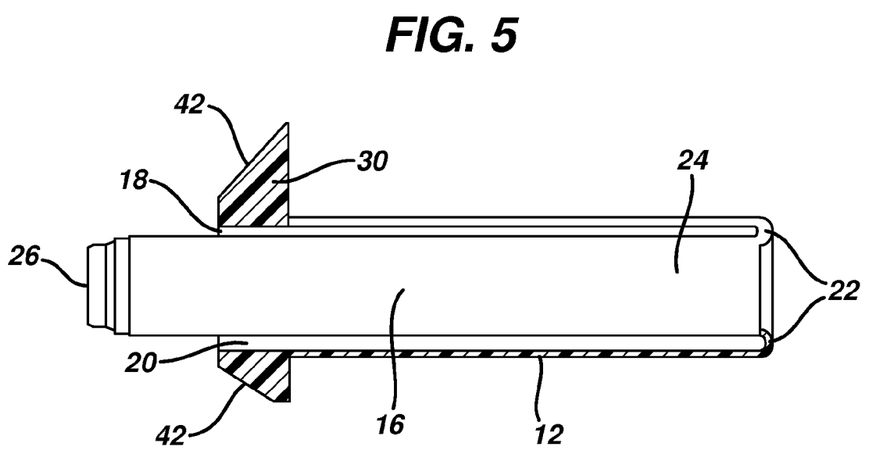
FIG. 5 is a cross-section of the handle of FIG. 4, taken along line 5-5.
Figure 6:
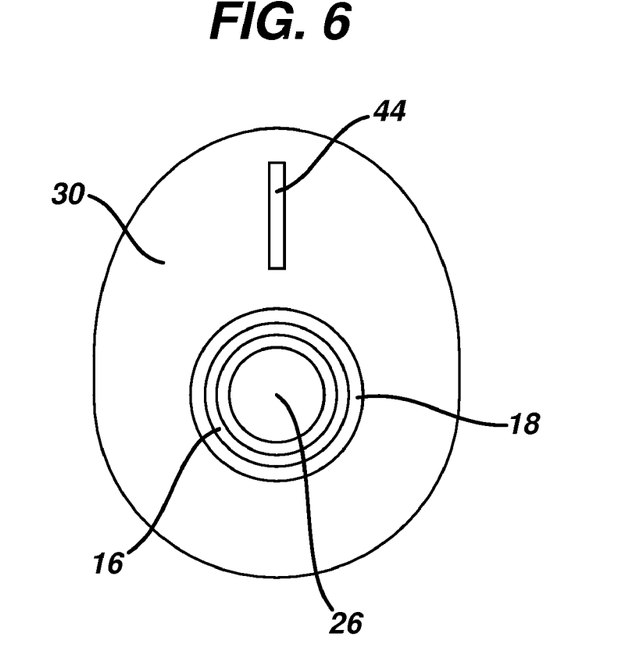
FIG. 6 is a front view of the handle of FIG. 4.

The elongate handle 12 can take on various forms, including tubular and the like. The cavity 20 is dimensioned and configured to accept the insertion sleeve 14 as the sleeve 14 is drawn into the cavity 20. In the event that the elongate handle 12 is of a tubular nature, the interior of the tubular structure forms at least part of the cavity 20. This is shown in FIGS. 2 and 3. The handle 12 is shown separately and in more detail in FIGS. 4-6. The cavity 20 is also connected to the exterior of the elongate handle 12 through an aperture 28 to permit manipulation of the insertion sleeve 14 from outside of the handle 12. Preferably, the aperture 28 is elongated, such as the slot shown in FIG. 4. The elongate handle may also include an insertion depth indicator 30 that may be in a fixed position or adjustable.

Figure 7:
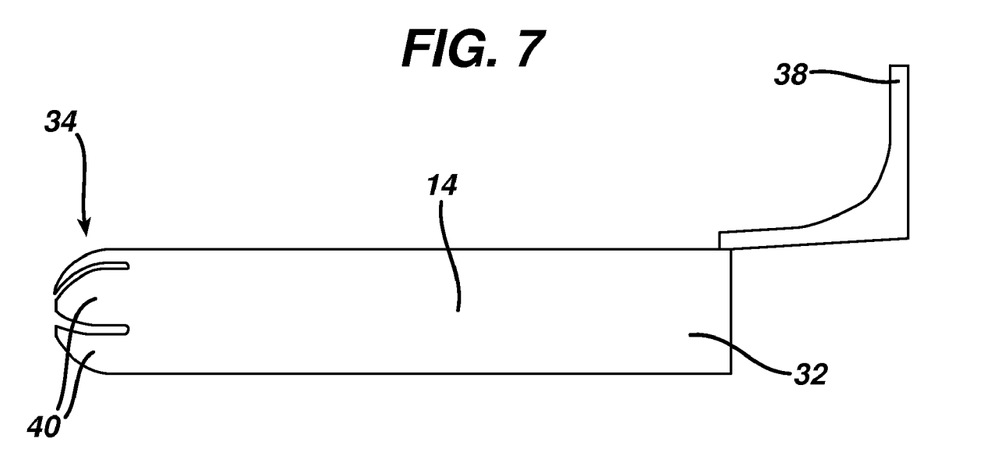
FIG. 7 is a side elevation of an insertion sleeve of an applicator according to the present invention.

The insertion sleeve 14 is shown separately in FIG. 7. The sleeve 14 has a base portion 32 contained within the handle 12, and it extends from the open first end 18 of the handle 12, terminating in an insertion end 34 disposed distal the handle 12. The sleeve 14 is arranged and configured to slide into the handle 12 and to accommodate the intravaginal device 36 to be delivered. The base portion 32 has a trigger 38 operatively connected thereto.

Again, the insertion sleeve is sized and shaped to contain the urinary incontinence device 36 within it. The insertion sleeve may have a length of about 35 mm to 135 mm. The diameter of the sleeve may range from 5 mm to 20 mm. The thickness of the sleeve is such that the sleeve can withstand pressure exerted by the device, and may range, for example, from 1 mm to 3 mm. The insertion end 34 may be open, or as is known in the tampon art, may have petals 40 for easing insertion of the applicator and for retaining the device until deployment.

The insertion sleeve may be made from any suitable material, such as polyethylene, polypropylene, acetal resins, styrene copolymers (including rubber-modified glassy plastics such as ABS [a two-phase system of styrene-acrylonitrile copolymer and styrene-budatidene copolymer]). The insertion depth indicator may be molded into the barrel or may be formed separately and attached to the applicator through conventional methods, such as adhesives, friction fits and the like.

The insertion depth indicator 30 is a raised element on the handle, oriented generally perpendicular to the longitudinal axis of the handle (and thus, the direction of insertion). This provides a tactile feedback when the applicator is fully inserted into the user's vagina. While a small height of discontinuity is sufficient to give a tactile feedback, the height of the discontinuity also defines a bearing surface 42 that can be held against the body to maintain the correct insertion depth during deployment of the device. The height of the discontinuity may range from 2 mm to 20 mm.

The insertion depth indicator may be made from any suitable material, such as polyethylene, polypropylene, a variety of copolymers, silicone, and elastomeric materials, such as ethylene propylene diene monomer and the like. The insertion depth indicator may be molded into the barrel or may be formed separately and attached to the applicator through conventional methods, such as adhesives, friction fits and the like.

The insertion depth indicator may also function as and/or incorporate a finger grip. The insertion depth indicator is positioned such that the device is deployed in the proper position within the vagina. The distance between the base of petals at the insertion end of the sleeve 14 and the insertion depth indicator 30 may range from 40 cm to 80 cm, for example 65 mm. The amount that the insertion depth indicator extends about the circumference of the insertion sleeve, the "angle of wrap" may vary. An angle of wrap of 360° shown in the structure of the figures provides the largest and most stable bearing surface 42; however, smaller angles require less material and can be more convenient to stack and store.

The insertion depth indicator 30 aids in the correct placement of the intravaginal device 36. The indicator is placed against a woman's labia as an indication to the correct depth to insert the barrel of the applicator into the body. As the labia have a curved shape, the indicator or collar may also be designed to curve upwards to be placed close against and a little between the labia. The angle of curvature from the vertical line of the applicator may be about 10 degrees. The bearing surface 42 can also consist of multiple segments spaced around the circumference of the insertion sleeve. Each of such multiple segments may also have a different height.

The external depth indicator may be integral with the sleeve (including permanently and immovably attached), or it may be adjustable, if desired. This may be helpful to improve comfort for the user. A woman may desire to change the location of the indicator 30 along the length of the handle 12 if she desires to fine-tune the insertion depth based upon her knowledge of her own anatomy. To aid in this adjustment, indicia may be provided on the handle 12.

Figure 8:
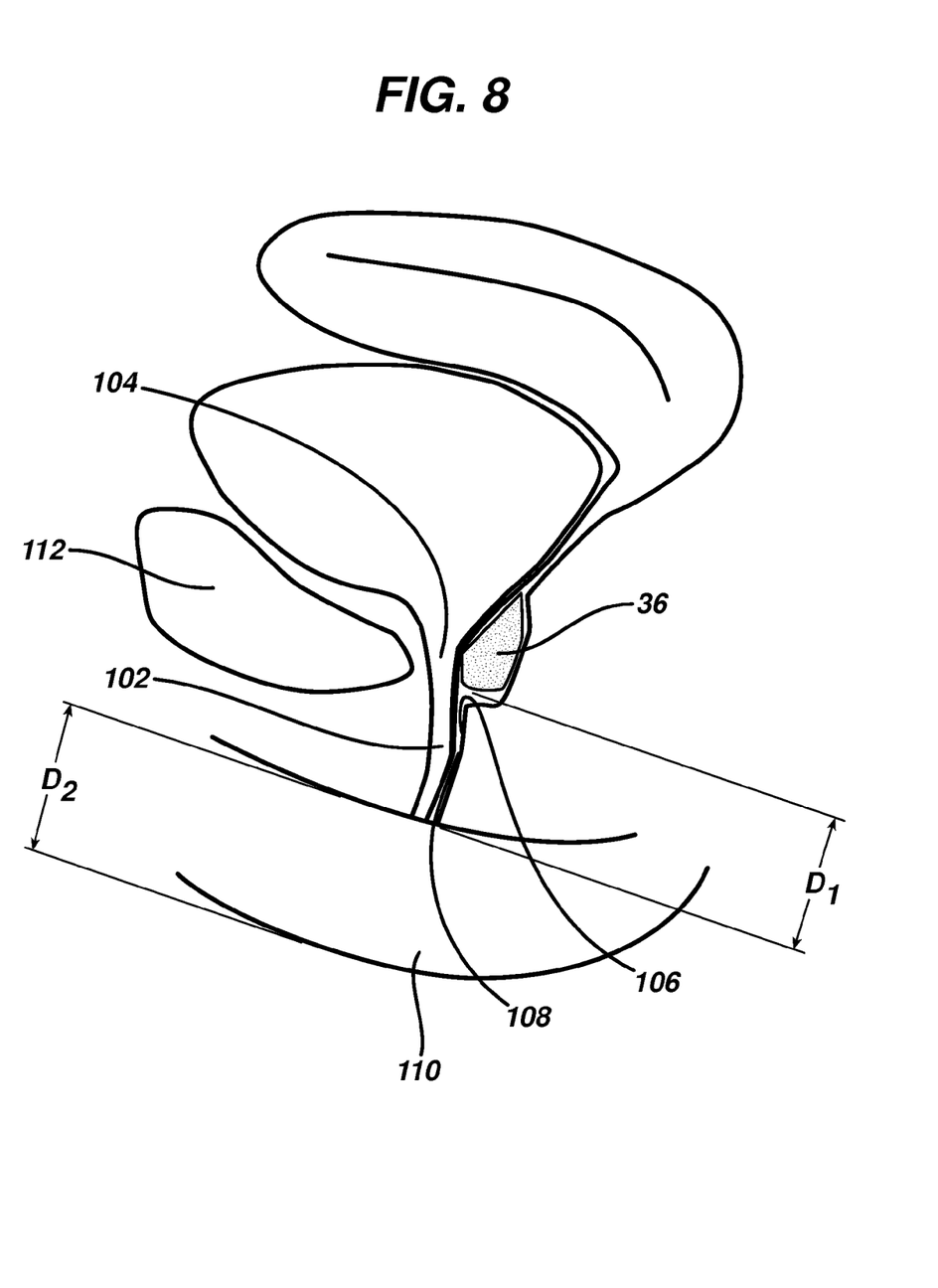
FIG. 8 is a sagittal cross-section of the female pelvis illustrating relationship between the vagina, bladder, urethra, pubic bone, urethro-vesical junction, and labia.

As shown in FIG. 8, the applicator is designed so that the portion of the device 36 in the vagina that applies pressure to the urethra 102 is placed at the urethro-vesical junction 104, and/or the base 106 of the device 36 is at least 10 mm to 20 mm, for example 15 mm above the hymenal opening 108 (dimension $D_1$). To this dimension is added the distance $D_2$ between the outer surface of the labia majora 110 and the hymenal opening 108.

If desired, the applicators according to the present invention may also include an orientation indicator 44 to supplement the orientation guide that the trigger 38 may provide. The orientation indicator 44 is utilized to place the incontinence device in the vagina such that when it is deployed, the portion of the device that applies pressure exerts pressure on the urethra-vesical junction, and any anchoring members lie on the lateral sides of the vagina. The orientation indicator 44 clearly marks the orientation of the device within the applicator. The indicator may be a raised line, a colored line, dots, embossments, or any suitable mark or shape that indicates orientation. The orientation indicator may be on any or all of a conventional finger grip, the insertion depth indicator, and the sleeve itself. If the device is aligned with the orientation indicator when it is within the applicator, then it will be aligned to the body after insertion. When the orientation indicator 44 is part of the insertion depth indicator 30, the orientation indicator 44 may be part of the shape of the insertion depth indicator 30. For example, the insertion depth indicator 30 may have an apex, which is the indicator.

In use, a woman can insert the insertion sleeve 14 into her vagina until the insertion depth indicator 30 contacts her labia majora. She may then move the trigger 38 away from her body, which moves a substantial portion of the insertion sleeve 14 into the cavity 20 of the handle 12. When the trigger 38 reaches the end of the slot 28, the intravaginal device support member 16 will have maintained the intravaginal device 36 within the vagina at an appropriate location for it to provide the desired benefit. The applicator 10 may then be removed from her body, leaving the intravaginal device in place. This action has the significant benefit of reducing or even eliminating the need to move the intravaginal device within the vagina. This helps to place the device in a safe, non-abrasive, and comfortable manner. Due to the high expansion forces of the incontinence device, a conventional push style applicator would push the device out of the applicator and slide it along the vaginal epithelium. This present applicator places the device in its correct location in the vagina by withdrawing the elongate insertion sleeve off the device, instead of pushing it in place.

Figure 9:
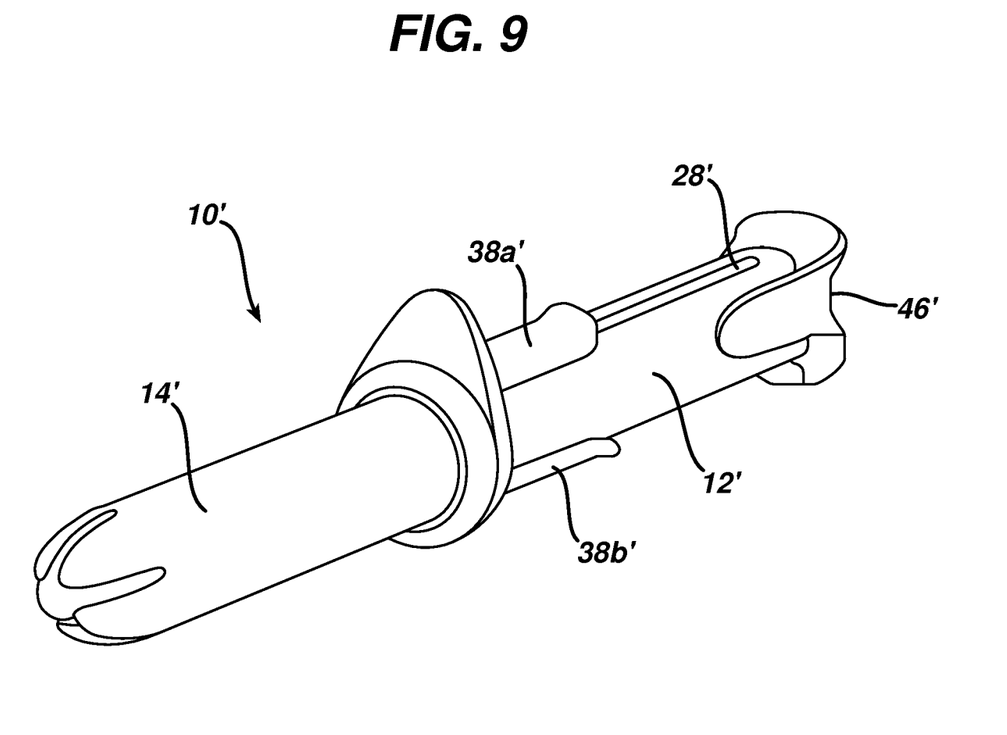
FIG. 9 is a perspective view of an alternative embodiment of the applicator of the present invention.

In use of the alternative embodiment of FIG. 9, a woman can hold the applicator 10' with her fingers on the trigger (two finger pads 38a' and 38b') extending from the insertion sleeve 14' and her forefinger on the end 46' of the handle 12'. She may then insert the insertion sleeve 14' into her vagina until the insertion depth indicator 30' contacts her labia majora. She may then move the finger pads 38a' and 38b' away from her body, which moves a substantial portion of the insertion sleeve 14' into the cavity of the handle 12'. This arrangement provides the appearance of pushing the end of the handle when the user is actually pulling the insertion sleeve 14'. When the finger pads 38a' and 38b' reach the end of the slot 28', the intravaginal device support member will have maintained the intravaginal device within the vagina at an appropriate location for it to provide the desired benefit. The applicator 10' may then be removed from her body, leaving the intravaginal device in place.

Suitable urinary incontinence devices for use with the applicators of the present invention include, but are not limited to, devices taught in co-pending US Patent Applications, U.S. application Ser. No. 11/456,376, filed, Jul., 10, 2006; U.S. application Ser. No. 11/776,178, filed, Jul. 11, 2007; U.S. application Ser. No. 11/456,390, filed, Jul. 10, 2006; U.S. application Ser. No. 11/456,402, filed, Jul. 10, 2006; U.S. application Ser. No. 11/456,424, filed, Jul. 10, 2006; U.S. application Ser. No. 11/776,185, filed, Jul. 11, 2007; U.S. application Ser. No. 11/456,433, filed, Jul. 10, 2006; and U.S. application Ser. No. 11/456,442, filed, Jul. 10, 2006.

Examples are set forth below to further illustrate the nature of the invention and the manner of carrying it out. However, the invention should not be considered as being limited to the details thereof.

EXAMPLE 1

Figure 1:
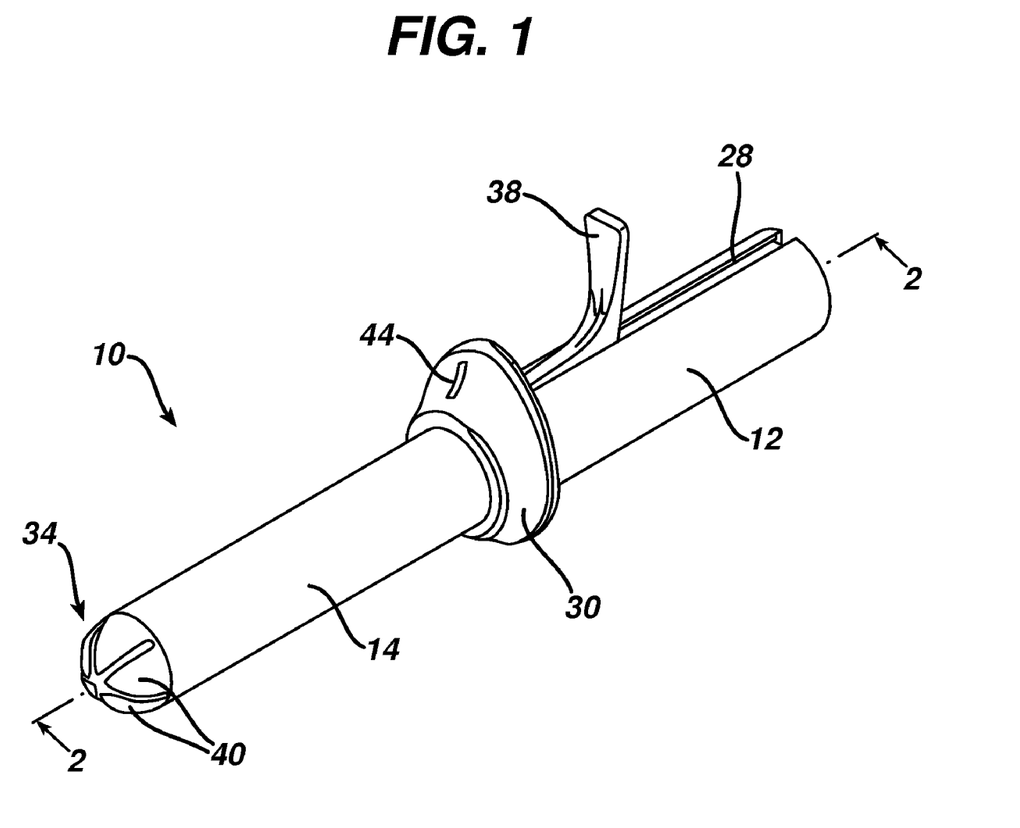
FIG. 1 is a perspective view of an applicator of the present invention.

Barrel and support member components according to FIG. 1 were molded out of linear low-density polyethylene (LLDPE) with a 1% modified polyethylene slip additive. Samples of these components were also molded out of high-density polyethylene (HDPE) and low-density polyethylene (LDPE). The LLDPE however was the material of choice for actual use testing. The collar and finger grip components also utilized single cavity injection molds. A finger-grip sleeve and the insertion depth indicator collar were both designed to be friction fit attached to the applicator, and the distance from the collar to the base of the petals was about 65 mm. The material utilized was a 65-durometer thermoplastic elastomer under the trade name of C-flex. The collar and the finger grip were both fit to the barrel such that they could be slid to different positions on the barrel that were associated with a woman's depth of labia associated with her BMI.

EXAMPLE 2

A use test was performed with 20 women to mainly determine the ability of the applicators of the present invention to correctly place the device in the body. An intra-vaginal incontinence device prototype was inserted into the vagina utilizing the applicator of Example 1. The first test was for the subject to insert the device via the provided applicator and instructions. For this test, a physician checked the placement of the device post insertion and assessed whether the device was too high, at the correct location, or too low.

Referring again to FIG. 8, the device 36 was considered to be too high if the base 106 of the device 36 was located above the urethro-vesical junction 104. This was assessed by palpation. If the doctor could feel the pubic bone 112 before the base 106 of the device 36, the device was considered to be too high. The device 36 was considered to be at the correct location if the working member of the device 36 was at the urethro-vesical junction 104. This was assessed by palpation or visualization. If the doctor could see that the device 36 was at least 10 mm into the vagina past the hymenal ring 108 or if the doctor could feel the base 106 of the device 36 before feeling the pubic bone 112, the device 36 was considered to be at the correct location. The device was considered to be too low if it was placed outside the hymenal ring 108 or less than 10 mm into the vagina past the hymenal ring 108.

If the device was placed incorrectly (too high or too low), the subject was asked to re-insert the device with feedback on the initial placement. The results of this study of placement via applicator are shown in Table 2 below.

TABLE 2

| Insertion | % With Correct Placement |
| --- | --- |
| Initial | 50 (10/20) |
| Second | 70 (7/10) |
| Total | 85 (17/20) |

Based on the data above, it was determined that the devices of the present invention are effective at placing urinary incontinence devices in the proper position within the vagina, either initially or with guidance and practice.

We claim:

1. An applicator for intravaginal devices comprising:
   a) an elongate handle having an open first end that defines a cavity extending into the handle and having an insertion depth indicator disposed proximate the open first end of the handle;
   b) an insertion sleeve that has a base portion contained in the handle and that extends from the open first end of the handle toward an insertion end disposed distal the handle, that is arranged and configured to slide into the cavity of the handle and to accommodate an intravaginal device, and that has associated therewith a trigger operatively connected to the base portion to activate movement of the insertion sleeve; and
   c) an intravaginal device support member that is disposed in the cavity of the handle, that is operatively connected to the handle, and that has a bearing surface disposed proximate the open first end of the handle;
   wherein the insertion end of the insertion sleeve defines an insertion end of the applicator, and the open first end of the elongate handle is disposed toward the insertion end of the applicator.

2. The applicator of claim 1, wherein the elongate handle comprises a tubular member, and the cavity is the interior of the tubular member.

3. The applicator of claim 2, wherein the tubular member has a longitudinal slot through which the trigger projects.

4. The applicator according to claim 1 wherein the insertion depth indicator is adjustable.

5. An applicator for intravaginal devices comprising:
   a) an elongate tubular handle having an open first end and a longitudinal slot;
   b) an elongate insertion sleeve that has a base portion contained within the handle; that extends from the open first end of the handle, terminating in an insertion end disposed distal the handle; that is arranged and configured to slide into the tubular handle and to accommodate an intravaginal device; and that has a trigger operatively connected to the base portion, wherein the trigger is capable of activating movement of the insertion sleeve; and c) an intravaginal device support member that is disposed in the handle, that is operatively connected to the handle distal the open end thereof, and that has a bearing surface disposed proximate the open first end of the handle;

wherein the insertion end of the insertion sleeve defines an insertion end of the applicator, and the open first end of the elongate handle is disposed toward the insertion end of the applicator.

6. The applicator of claim 5, wherein the elongate handle further comprises an insertion depth indicator.

7. The applicator according to claim 6 wherein the insertion depth indicator is adjustable.

8. The applicator according to claim 1, wherein the insertion sleeve further comprises petals at an insertion end disposed opposite the base portion.

9. The applicator according to claim 5, wherein the insertion end of the elongate insertion sleeve further comprises petals.

* * * * *